US011186815B2

(12) United States Patent
Lee et al.

(10) Patent No.: US 11,186,815 B2
(45) Date of Patent: Nov. 30, 2021

(54) **METHODS OF USING *LACTOBACILLUS PLANTARUM* STRAINS FOR PROTECTING ANIMALS FROM PATHOGENIC BACTERIAL INFECTION**

(71) Applicant: Nutraferma, Inc., Sioux City, IA (US)

(72) Inventors: Chan Ho Lee, Chungcheongnam-Do (KR); Jung Sun Kang, Chungcheongnam-Do (KR); Won Tak Cho, Chungcheongnam-Do (KR); Kyung Jin Cho, Chungcheongnam-Do (KR); Eric Lohry, Sioux City, IA (US)

(73) Assignee: Nutraferma, Inc., Sioux City, IA (US)

( * ) Notice: Subject to any disclaimer, the term of this patent is extended or adjusted under 35 U.S.C. 154(b) by 502 days.

(21) Appl. No.: 16/007,339

(22) Filed: Jun. 13, 2018

(65) Prior Publication Data
US 2018/0362919 A1 Dec. 20, 2018

Related U.S. Application Data

(60) Provisional application No. 62/519,499, filed on Jun. 14, 2017.

(51) Int. Cl.
| | |
|---|---|
| A23L 33/135 | (2016.01) |
| A23K 50/00 | (2016.01) |
| C12N 1/20 | (2006.01) |
| A23K 50/75 | (2016.01) |
| A23K 10/18 | (2016.01) |
| A61K 35/747 | (2015.01) |
| A23K 50/10 | (2016.01) |
| A23K 50/30 | (2016.01) |
| A61K 35/00 | (2006.01) |
| C12R 1/25 | (2006.01) |

(52) U.S. Cl.
CPC ............... *C12N 1/20* (2013.01); *A23K 10/18* (2016.05); *A23K 50/10* (2016.05); *A23K 50/30* (2016.05); *A23K 50/75* (2016.05); *A61K 35/747* (2013.01); *C12N 1/205* (2021.05); *A23L 33/135* (2016.08); *A61K 2035/115* (2013.01); *C12R 2001/25* (2021.05)

(58) Field of Classification Search
CPC ........ A23K 10/18; A23K 50/30; A23K 50/10; A23K 50/75; C12N 1/20; A61K 2035/115; A61K 35/747; A23L 33/135; C12R 1/25
See application file for complete search history.

(56) References Cited

U.S. PATENT DOCUMENTS

| 5,494,664 A | 2/1996 | Brassart et al. |
| 7,323,166 B2 | 1/2008 | Brashears et al. |
| 9,492,487 B2 | 11/2016 | Garner et al. |
| 2011/0189132 A1* | 8/2011 | Garner et al. ............... 424/93.3 |
| 2013/0296165 A1* | 11/2013 | Harel et al. ............ A61K 47/42 504/100 |

FOREIGN PATENT DOCUMENTS

| EP | 0768375 A1 | 4/1997 |
| KR | 10-0808910 B1 | 3/2008 |
| KR | 20120064416 A | 6/2012 |
| KR | 20140022506 A | 2/2014 |
| KR | 20150130066 A | 11/2015 |
| KR | 10201700730222 A | 6/2017 |
| WO | WO-2016/064000 A1 | 4/2016 |

OTHER PUBLICATIONS

Kumaree K. K. et al., "Bioencapsulation and application of Lactobacillus plantarum from catfish gut as an antimicrobial agent and additive in fish feed pellets", Ann. Microbiol., 2015, vol. 65, pp. 1439-1445. (Year: 2015).*
Foltz, K. L., et al., "Efficacy of *Lactobacillus plantarum* Supplementation in Broilers Challenged with Avian Pathogenic *Escherichia coli* and *Salmonella typhimurium*," J. Appl. Poult. Res., 2017, vol. 26, pp. 316-324.
Heilig, H. G., et al., "Molecular Diversity of *Lactobacillus* spp. and Other Lactic Acid Bacteria in the Human Intestine as Determined by Specific Amplification of 16S Ribosomal DNA," Appl. Environ. Microbiol., 2002, vol. 68, No. 1, pp. 114-123.
International Search Report Issued in PCT/US2018/037345 dated Jan. 21, 2019.
Written Opinion of the International Searching Authority Issued in PCT/US2018/037345 dated Jan. 21, 2019.
International Preliminary Report on Patentability dated Dec. 26, 2019 in corresponding International Application No. PCT/US2018/037345, and Notification Concerning Transmittal of International Preliminary Report on Patentability (Chapter 1 of the Patent Cooperation Traty).
New probiotic changes what we know about probiotic use in pelleted feed. All About Feed (Gateway to the global feed industry), Feed Additives, Article. Jan. 21, 2016 [online], [retrieved on May 17, 2020]. Retrieved from the Internet <URL: <https://www.allaboutfeed.net/animal-feed/feed-additives/new-probiotic-changes-what-we-know-about-probiotic-use-in-pelleted-feed/>>.
Kung, LJ 1998. Direct-fed microbials and enzymes for dairy cows. In Mid-south ruminant nutrition conference (ed. ER Jordan), pp. 69-77. Dallas-Forth Worth, Texas.

* cited by examiner

*Primary Examiner* — Satyendra K Singh
(74) *Attorney, Agent, or Firm* — Faegre Drinker Biddle & Reath LLP

(57) ABSTRACT

Disclosed are new uses of lactic acid bacteria, in particular *Lactobacillus plantarum*, for protecting animals from pathogenic bacterial infection, specifically, methods for reducing the mortality rate of animals against infection of pathogenic bacteria, methods for reducing the growth of pathogenic bacteria in the gastrointestinal tract of the animals, as well as methods of increasing and/or stimulating immune system of the animal through the use of such lactic acid bacteria.

20 Claims, 7 Drawing Sheets

Specification includes a Sequence Listing.

METHODS OF USING *LACTOBACILLUS PLANTARUM* STRAINS FOR PROTECTING ANIMALS FROM PATHOGENIC BACTERIAL INFECTION

CROSS-REFERENCE TO RELATED APPLICATIONS

This application claims priority to U.S. provisional application No. 62/519,499 filed on Jun. 14, 2017, the entire content of which is incorporated herein by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_213889_0001. The size of the text file is 3 KB, and the text file was created on Jun. 13, 2018.

TECHNICAL FIELD

Disclosed are new uses of lactic acid bacteria, in particular *Lactobacillus plantarum*, for protecting animals from pathogenic bacterial infection, specifically, methods for reducing the mortality rate of animals against infection of pathogenic bacteria, methods for reducing the growth of pathogenic bacteria in the gastrointestinal tract of the animals, as well as methods of increasing and/or stimulating immune system of the animal through the use of such lactic acid bacteria.

BACKGROUND

Organisms that produce lactic acid as a major metabolic component have been known for a long time. These bacteria may be found in milk or milk processing factories, living or decaying plants, but also in the intestines of man and animals. These microorganisms, collectively named "lactic acid bacteria," represent a rather inhomogeneous group and comprise, for instance, the genera *Lactococcus, Lactobacillus, Streptococcus, Bifidobacterium*, and *Pediococcus*.

Lactic acid bacteria have recently attracted a great deal of attention in that some strains have been found to exhibit valuable properties to man and animals upon ingestion. In particular, specific strains of the genus *Bifidobacterium* or *Lactobacillus* have been found to be able to colonize the intestinal mucosa and to assist in the maintenance of the well-being of man and animal. These lactic acid bacteria are also referred to as "probiotics" or "direct-fed microbials."

For instance, EP 0 768 375 discloses specific strains of the genus *Bifidobacterium* that are capable of becoming implanted in the intestinal flora and may adhere to intestinal cells. These *Bifidobacteria* are reported to assist in immunomodulation and being capable of competitively excluding adhesion of pathogenic bacteria to intestinal cells, thus assisting in the maintenance of the individual's health.

Likewise, U.S. Pat. No. 9,492,487 discloses specific strains of the genus *Lactobacillus* that are capable of reducing or inhibiting populations of pathogenic bacteria in the gastrointestinal tract of an animal. These *Lactobacillus* strains are reported to be useful as probiotic microorganisms for improving animal health and/or productivity.

Despite the numerous strains of lactic acid bacteria that are currently available, there remains a desire in the art for additional lactic acid bacterial strains that are beneficial to the well-being of man and/or animal. Particularly, there remains a need for additional lactic acid bacterial strains having antimicrobial activity against pathogenic bacteria that can be used as direct-fed microbials as supplements to basal diet feeds or feedstock. There also remains a need for additional lactic acid bacterial strains that are heat-stable and shelf-stable so that they may be pelleted into feed.

SUMMARY

According to an embodiment, disclosed is a method for protecting an animal from pathogenic bacterial infections by administering to the animal a basal diet feed supplemented with a direct-fed microbial comprising *Lactobacillus plantarum*. In particular, the method comprises administering to the animal a basal diet feed supplemented with at least 0.01% by weight of a direct-fed microbial comprising *Lactobacillus plantarum* for a period of at least 7 days so that, when infected by a pathogenic bacterium, the animal has a lower mortality rate as compared to a corresponding control animal that is not fed with such a direct-fed microbial. In some embodiments, the growth of pathogenic bacteria in the gastrointestinal tract of the animal fed with such a direct-fed microbial is reduced. In other embodiments, the immune system of the animal fed with such a direct-fed microbial is increased as compared to a corresponding control animal that is not fed with the direct-fed microbial.

In some embodiments, the animal is a cattle, pig, or poultry, which includes but are not limited to broilers and egg-producing chickens. In other embodiments, the pathogenic bacterium is *Escherichia coli*, including avian pathogenic *Escherichia coli, Salmonella typhimurium, Salmonella enteritidis*, and/or *Clostridium perfringens*. In some preferred embodiments, the *Lactobacillus plantarum* is the *Lactobacillus plantarum* strain deposited in Korean Culture Center of Microorganisms (KCCM) under Accession No. KCCM 11258P and/or the *Lactobacillus plantarum* strain deposited in Korean Culture Center of Microorganisms (KCCM) under Accession No. KCCM 11453P. Preferably, the *Lactobacillus plantarum* is grown and concentrated by fermentation, such as solid state fermentation, on a feed grain substrate. In some embodiments, the basal diet feed comprising *Lactobacillus plantarum* as direct-fed microbial may be pelleted.

According to another embodiment, disclosed is a method for reducing mortality rate of poultry against infection of avian pathogenic *Escherichia coli, Salmonella typhimurium, Salmonella enteritidis*, and/or *Clostridium perfringens* by administering to the poultry a basal diet feed supplemented with a direct-fed microbial comprising *Lactobacillus plantarum*. Particularly, the method comprises administering to the poultry a basal diet feed supplemented with at least 0.01% by weight of a direct-fed microbial comprising *Lactobacillus plantarum* for a period of at least 7 days so that, when infected by avian pathogenic *Escherichia coli, Salmonella typhimurium, Salmonella enteritidis*, and/or *Clostridium perfringens*, the poultry has a lower mortality rate as compared to a corresponding control poultry that is not fed with such a direct-fed microbial.

In some embodiments, the poultry is a broiler chicken or an egg-producing chicken. In other embodiments, the *Lactobacillus plantarum* is the *Lactobacillus plantarum* strain deposited in Korean Culture Center of Microorganisms (KCCM) under Accession No. KCCM 11258P and/or the *Lactobacillus plantarum* strain deposited in Korean Culture Center of Microorganisms (KCCM) under Accession No. KCCM 11453P. Preferably, the *Lactobacillus plantarum* is grown and concentrated by fermentation, such as solid state fermentation, on a feed grain substrate. In some embodiments, the basal diet feed comprising *Lactobacillus plantarum* as direct-fed microbial may be pelleted.

According to yet another embodiment, disclosed is a method for reducing the growth of pathogenic bacteria in the gastrointestinal tract of an animal by administering to the animal a pelleted basal diet feed supplemented with at least 0.01% by weight of a direct-fed microbial comprising at least one specific strain of *Lactobacillus plantarum* that is grown and concentrated by a solid state fermentation process using a feed grain substrate. Preferably, the at least one specific strain of *Lactobacillus plantarum* used in such a method is the *Lactobacillus plantarum* strain deposited in Korean Culture Center of Microorganisms (KCCM) under Accession No. KCCM 11258P and/or the *Lactobacillus plantarum* strain deposited in Korean Culture Center of Microorganisms (KCCM) under Accession No. KCCM 11453P.

In some embodiments, the animal is a cattle, pig, or poultry, which includes but are not limited to broilers and egg-producing chickens. In other embodiments, the pathogenic bacterium is *Escherichia coli, Salmonella typhimurium, Salmonella enteritidis*, and/or *Clostridium perfringens*.

DETAILED DESCRIPTION

Figure 1:
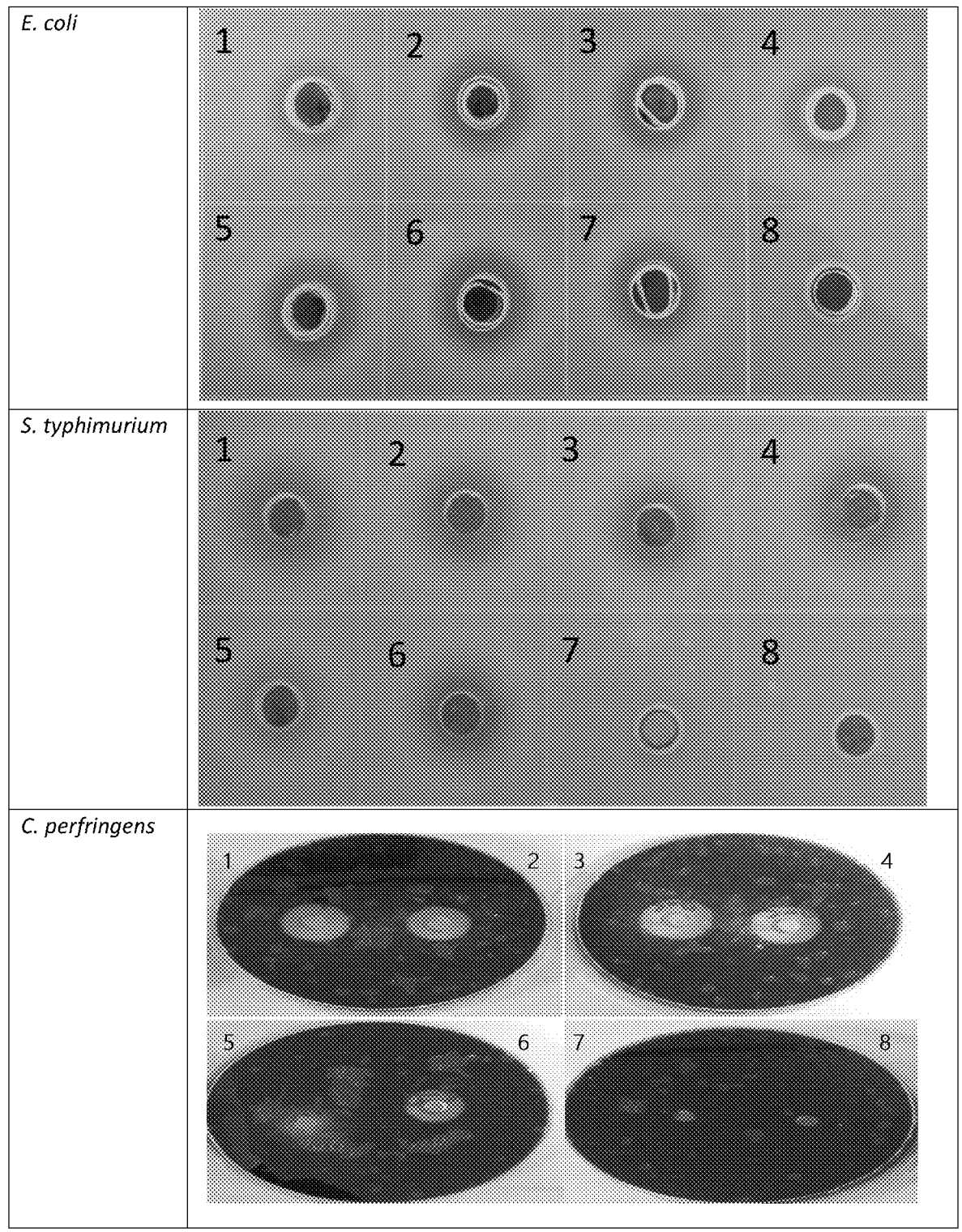
FIG. 1 shows the antimicrobial activity of *Lactobacillus plantarum* strains KCCM 11258P and KCCM 11453P (1: *Lactobacilus plantarum* strain KCCM 11258P; 2-5 and 7: *Lactobacilus plantarum*; 6: *Lactobacilus plantarum* strain KCCM 11453P; 8: negative control with distilled water).

All publications, patents and patent applications, including any drawings and appendices, herein are incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the claims, or that any publication specifically or implicitly referenced is prior art.

The present application relates to new uses of lactic acid bacteria, in particular *Lactobacillus plantarum*, as direct-fed microbials for protecting animals from pathogenic bacterial infection. Direct-fed microbials are used in animal health applications in order to maintain healthy gut microflora. The modes of action of direct-fed microbials may include lactic acid fermentation, production of bacteriocins, organic acids, and hydrogen peroxide, competitive exclusion of pathogenic bacteria, increased digestive enzyme activity, and stimulation of the immune system. Several specific strains of the genus *Bifidobacterium* or *Lactobacillus* have been identified as good candidates for direct-fed microbials due to their capability to colonize the intestinal mucosa and to assist in the maintenance of the well-being of man and animal.

The genus *Lactobacillus* includes the most prevalently administered probiotic bacteria (Flint et al., Journal of Microbiological Methods, 2005, 61: 235-243). *Lactobacillus* is a genus of gram-positive, facultative anaerobic or microaerophilic, rod-shaped, non-spore-forming bacteria. The genus *Lactobacillus* currently contains over 180 species and encompasses a wide variety of organisms (Wikipedia "*Lactobacillus*" as of April 2017). *Lactobacillus* species are often used in the manufacture of food products including dairy products and other fermented foods.

*Lactobacillus* species inhabit various locations including the gastrointestinal tracts of animals and intact and rotting plant material (see e.g., Heilig et al., Applied and Environmental Microbiology, 2002, 68: 114-123; U.S. Pat. No. 7,323,166). *Lactobacillus* strains appear to be present in the gastrointestinal tract of approximately 70% of humans that consume a Western-like diet (Heilig et al., 2002).

*Lactobacillus plantarum* is a widespread member of the genus *Lactobacillus*, commonly found in many fermented food products as well as anaerobic plant matter. Various strains of *Lactobacillus plantarum* isolated from poultry have been identified as good candidates for direct-fed microtias in in vitro studies because of their antimicrobial activity against several pathogens, tolerance of bile and low pH, and adhesion to enterocytes (Foltz et al., J. Appl. Poult. Res., 0: 1-9, 2017). In searching for additional lactic acid bacteria strains for use as direct-fed microbials to supplement basal diet feeds or feedstock, it was surprising and unexpected to find that certain strains of *Lactobacillus plantarum* not only have excellent antimicrobial activity against pathogenic bacteria, but also ability to withstand high temperature used in pelleting feeds (e.g., 95° C.), which makes them good candidates for direct-fed microbials to be pelleted into feeds for use in animal diets.

According to an embodiment, there is a method for protecting animal from pathogenic bacterial infection by reducing the mortality rate of animals against infection of pathogenic bacteria through the use of such *Lactobacillus plantarum* strains. The method reduces the mortality rate of poultry against infection of avian pathogenic *Escherichia coli, Salmonella typhimurium, Salmonella enteritidis*, and/or *Clostridium perfringens* through the use of such *Lactobacillus plantarum* strains. In one aspect, the method reduces the growth of pathogenic bacteria in the gastrointestinal tract of the animals through the use of such *Lactobacillus plantarum* strains. In another aspect, the method increases and/or stimulates the immune system of the animal through the use of such *Lactobacillus plantarum* strains.

The methods comprise administering to the animal a basal diet feed that is supplemented with a direct-fed microbial comprising *Lactobacillus plantarum*. Preferably, the basal diet feed that is supplemented with a direct-fed microbial comprising *Lactobacillus plantarum* is pelleted.

In general, the methods may be used for all non-human and non-insect animals. Animals that may benefit from the methods of the present application include but are not limited to birds, swine, ruminants, pets and exotic animals, zoo animals, aquatic animals, and horses, among others. In some embodiments, the animals are farm animals raised for consumption or as food-producers, such as cattle, pigs or poultry. In other embodiments, the animals are broilers or egg-producing chickens.

According to an embodiment, the amount of a direct-fed microbial comprising *Lactobacillus plantarum* used to supplement the basal diet feed should be such so that it is sufficient to reduce the mortality rate of animals upon infection by pathogenic bacteria, to reduce the growth of pathogenic bacteria in the gastrointestinal tract of the animals, and/or to increase and/or stimulate the immune system of the animal. In some embodiments, the basal diet feed is supplemented with at least 0.01% by weight, preferably at least 0.05% by weight, more preferably at least 0.1% by weight, even more preferably 0.2% by weight, of a direct-fed microbial comprising *Lactobacillus plantarum*. In other embodiments, the basal diet feed is supplemented with less than 0.01% by weight or more than 0.2% by weight of a direct-fed microbial comprising *Lactobacillus plantarum*.

The basal diet feed supplemented with a direct-fed microbial comprising *Lactobacillus plantarum* may be administered to an animal over multiple days throughout the animal's life or during particular stages or portions of the animal's life. For instance, the basal diet feed supplemented with a direct-fed microbial comprising *Lactobacillus plantarum* may be administered only in a starter diet or only in a finisher diet of farm animals. In some embodiments, the basal diet feed supplemented with a direct-fed microbial comprising *Lactobacillus plantarum* is administered to the animal as a starter diet and continues throughout the animal's life. In other embodiments, the basal diet feed supplemented with a direct-fed microbial comprising *Lactobacillus plantarum* is administered to the animal only during portion(s) of the animal's life, preferably for a period of at least 3 days, more preferably for a period of at least 5 days, even more preferably for a period of at least 7 days. In some other embodiments, the basal diet feed supplemented with a direct-fed microbial comprising *Lactobacillus plantarum* may be administered to the animal for a period of less than 3 days or for a period of more than 7 days.

Suitable *Lactobacillus plantarum* strains to be used in the methods include but are not limited to the *Lactobacillus plantarum* strains that have antimicrobial activity against pathogenic bacteria, tolerance of bile and low pH, and adhesion to enterocytes. Preferably, the *Lactobacillus plantarum* strains used in the methods also have the ability to withstand high temperature used in a feed pelleting process, such as 95° C., so that it is possible to pellet the *Lactobacillus plantarum* strain(s) into feeds for use in animal diets. In some embodiments, the *Lactobacillus plantarum* strain used in the methods may comprise the strain deposited under the provisions of the Budapest treaty with Korean Culture Center of Microorganisms (KCCM), 361-221, Yurim B/D, Hongje-1-dong, Seodaemun-gu, Seoul 120-091, Republic of Korean on Feb. 20, 2012 under Accession No. KCCM 11258P. In other embodiments, the *Lactobacillus plantarum* strain used in the methods may comprise the strain deposited under the provisions of the Budapest treaty with Korean Culture Center of Microorganisms (KCCM), Yurim B/D, 45, Hongjenae-2ga-gil, Seodaemun-gu, Seoul 120-861, Republic of Korean on Sep. 13, 2013 under Accession No. KCCM 114531. In yet other embodiments, both the *Lactobacillus plantarum* strains KCCM 11258P and KCCM 11453P may be used together as direct-fed microbials in the methods.

The *Lactobacillus plantarum* strain(s) to be used in the methods may be obtained by culturing the *Lactobacillus plantarum* strain(s) according to methods well known in the art. Conventional microbial culture processes, such as submerged fermentation, solid state fermentation, or liquid surface culture, may be used. In some embodiments, the *Lactobacillus plantarum* strain(s) used in the methods may be grown and concentrated by fermentation, preferably by solid state fermentation, more preferably by solid state fermentation on a feed grain substrate. Methods for solid state fermentation of *Lactobacillus plantarum* on a feed grain substrate are described in, for example, KR101418820B1, which is hereby incorporated by reference.

The methods may be used to increase weight gain of an animal, to increase feed utilization efficiency, to reduce mortality, to increase disease resistance, to increase survival rates, and to increase the immune response of the animal, particularly upon infection of pathogenic bacteria. In some embodiments, the methods are used to reduce the mortality rate of animals, such as poultry, against infection of pathogenic bacteria, including but not limited to pathogenic *Escherichia coli*, *Salmonella typhimurium*, *Salmonella enteritidis*, and/or *Clostridium perfringens*. Preferably, the methods are used to reduce the mortality rate of poultry against infection of avian pathogenic *Escherichia coli*, *Salmonella typhimurium*, *Salmonella enteritidis*, and/or *Clostridium perfringens*. In other embodiments, the methods are used to reduce the growth of pathogenic bacteria, including but not limited to pathogenic *Escherichia coli*, *Salmonella typhimurium*, *Salmonella enteritidis*, and/or *Clostridium perfringens*, in the gastrointestinal tract of the animals. In yet some other embodiments, the methods are used to increase and/or stimulate the immune response of the animal upon infection of pathogenic bacteria, including but not limited to pathogenic *Escherichia coli*, *Salmonella typhimurium*, *Salmonella enteritidis*, and/or *Clostridium perfringens*.

Embodiments are further illustrated below by way of non-limiting examples.

EXAMPLES

Example 1 the Antimicrobial Activity of *Lactobacillus plantarum* Strains KCCM 11258P and Kccm 11453P The antimicrobial activity of *Lactobacillus plantarum* strains KCCM 11258P and KCCM 11453P against pathogenic bacteria *Escherichia coli*, *Salmonella typhimurium* and *Clostridium perfringens* was tested using the agar well diffusion method described below.

1.1 Preparation of *Lactobacillus plantarum*

The selected *Lactobacillus plantarum* strain was cultured in 100 ml MRS broth and incubated at 37° C. for 48 hours. The culture broth was centrifuged at 10,000 rpm for 20 minutes. The supernatant was then collected and filtered by passing through 0.25 µm sterile syringe filter (Whatman).

1.2 Preparation of Pathogenic Bacterium

The pathogenic bacterium (*Escherichia coli*, *Salmonella typhimurium* or *Clostridium perfringens*) was cultured in nutrient broth and incubated at 37° C. for 24 hours. The culture broth was centrifuged and the pellet obtained was suspended in 9 ml saline solution. The resultant suspension was used for inoculation of the pathogenic bacterium onto nutrient agar plates for the antimicrobial activity test.

1.3 Antimicrobial Activity Test

A lawn of the pathogenic bacterium was prepared by spreading the pathogenic bacterial suspension over the surface of nutrient agar plates with a sterile cotton swab. The plates were allowed to dry and a sterile cork borer of 9-mm diameter was used to cut uniform wells in the agar. Each well was then filled with 100 µl of culture-free filtrate obtained from the preparation of *Lactobacillus plantarum*. After incubation at 37° C. for 24 hours, each plate was examined for the presence of an inhibition zone around the well. If the diameter of the inhibition zone is greater than 1 mm, it is considered that the *Lactobacillus plantarum* strain tested has positive antimicrobial effect against the pathogenic bacterium tested. Each experiment was carried out in triplicate and the antimicrobial activity was reported as diameter of inhibition zone±SD in Table 1 below.

TABLE 1

Antimicrobial activity of the *Lactobacillus plantarum* strains KCCM 11258P and KCCM 11453P

| Pathogenic bacterium | Zone of inhibition (mm ± SD) | |
|---|---|---|
| | KCCM 11258P | KCCM 11453P |
| *Escherichia coli* | 23 (±1.8) | 24 (±1.9) |
| *Salmonella typhimurium* | 20 (±2.1) | 18 (±1.5) |
| *Clostridium perfringens* | 33 (±2.2) | 27 (±1.3) |

The antimicrobial activity of the *Lactobacillus plantarum* strains KCCM 11258P and KCCM 11453P in inhibiting the growth of the pathogenic bacteria tested may be due to the accumulation of main primary metabolites, such as lactic and acetic acids, ethanol and carbon dioxide. It may also due to the antimicrobial compounds that the *Lactobacillus plantarum* strains are capable of producing, such as formic and benzoic acids, hydrogen peroxide, diacetyl, acetoin and bacteriocins.

In this study, the agar well diffusion method was used to assess the antimicrobial activity of the *Lactobacillus plantarum* strains KCCM 11258P and KCCM 11453P. Their antimicrobial properties were tested against three major pathogenic bacteria, namely *Escherichia coli*, *Salmonella typhimurium* and *Clostridium perfringens*. Table 1 summarizes the results for the antimicrobial activity of the *Lactobacillus plantarum* strains tested. In conclusion, the *Lactobacillus plantarum* strains used for the antimicrobial activity test showed strong antimicrobial activity against *Escherichia coli*, *Salmonella typhimurium* and *Clostridium perfringens*.

Example 2 Efficacy of *Lactobacillus Plantarum* Supplementation in Broilers Challenged with Avian Pathogenic *Escherichia Coli*

Broilers were reared from day zero to 28 and orally challenged with $1 \times 10^8$ CFU of avian pathogenic *Escherichia coli* (APEC) on day 7. Treatments included a non-challenged positive control (PC), challenged negative control (NC), NC+0.05, 0.10, or 0.20% of a direct-fed microbial comprising the *Lactobacillus plantarum* strain KCCM 11258P (DFM), and NC+0.05% antibiotic (BMD). Body weight (BW) was not different among treatments. Mortality-corrected feed conversion ratio (FCRm) was increased with APEC challenge in comparison to the PC, while BMD returned FCRm to that of the PC ($P<0.05$). Treatment with 0.10% DFM resulted in the largest relative spleen weight (SW: % BW) at day 14, but also resulted in the lowest number of APEC associated mortalities, suggesting an enhanced immune response.

Example 3 Efficacy of *Lactobacillus plantarum* Supplementation in Broilers Challenged with *Salmonella typhimurium*

One-day-old broilers were orally challenged with $1 \times 10^8$ CFU of *Salmonella typhimurium* and fed a control diet (PC), or the same diet with 0.10% or 0.20% of a direct-fed microbial comprising the *Lactobacillus plantarum* strain KCCM 11258P (DFM). Intestinal samples were collected for determination of *Salmonella* colonization by the most probable number method at day 3 and day 7 post inoculation, and bioluminescence imaging using In-Vivo Imaging System at day 7 post inoculation. Treatment with DFM reduced total *Salmonella* content on day 7, but changes in bioluminescence were not significant.

Example 4 Efficacy of *Lactobacillus plantarum* Supplementation in Broilers Challenged with *Clostridium perfringens*

Broilers were assigned starting on day 1 post-hatch to dietary treatments for 0-23 days. The treatments consisted of non-challenged and challenged controls, a challenge control with BMD, and 3 levels of direct-fed microbial comprising the *Lactobacillus plantarum* strain KCCM 11258P (DFM) (0.05%, 0.10%, and 0.20%). Broilers were challenged with a live coccidiosis vaccine and *Clostridium perfringens* during week 2. Body weight (BW) was not significantly different among treatments. Mortality rate in broilers challenged with necrotic enteritis was 31%, while the non-challenged broilers had 0% mortality. The addition of BMD to the diets reduced the mortality to 3.6%, while the addition of DFM also reduced the mortality rate from 12.7% to 20% as compared to the control.

Example 5 Efficacy of *Lactobacillus plantarum* Supplementation in Laying Hens Challenged with *Salmonella enteritidis*

Thirty-two laying hens (46 weeks old at the beginning of the experiment) were housed individually in a wire layer cage under 16L:8D lightening schedule and fed with a commercial layer ration that either met or exceeded the requirement of laying hens performance. Hens were divided into groups to give 8 replicates per treatment that consisted of the treatments summarized in Table 2.

TABLE 2

Treatment groups and treatments

| Treatment Group (T) | Treatment |
|---|---|
| T1 | $SE^{NAR}$* unchallenged |
| T2 | $SE^{NAR}$ challenged |
| T3 | $SE^{NAR}$ challenged + 0.05% probiotics** |
| T4 | $SE^{NAR}$ challenged + 0.1% probiotics |

*$SE^{NAR}$ = chicken isolate of nalidixic acid resistant *Salmonella enteritidis*
**Probiotics = direct-fed microbial comprising the *Lactobacillus plantarum* strain KCCM 11453P Hens were off-fed for 10 hours after which they were challenged with $SE^{NAR}$. Feed was provided immediately after challenge.

Figure 4:
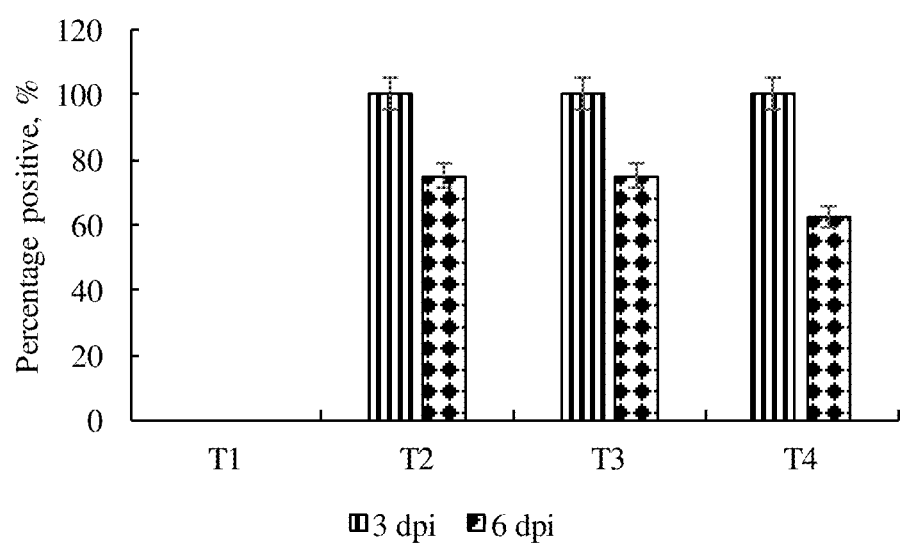
FIG. 4 shows the presence or absence of $SE^{NAR}$ in feces of laying hens challenged with $SE^{NAR}$ and supplemented with or without probiotics at 3 and 6 days post-infection (dpi). The treatment groups are: T1=$SE^{NAR}$ unchallenged, T2=$SE^{NAR}$ challenged, T3=$SE^{NAR}$ challenged+0.05% probiotics, and T4=$SE^{NAR}$ challenged+0.1% probiotics.

5.1 Effects of Probiotics and $SE^{NAR}$ in Colonization of Ceca, L/GB, Ovary, Spleen and Feces All hens were screened for fecal $SE^{NAR}$ shedding at 3 and 6 day post-infection (dpi). There was no significant difference between the fecal shedding on either 3 or 6 dpi, with incidence of positive feces higher at 3 dpi compared to 6 dpi (100 vs. 70-80%). As shown in FIG. 4, the percentage of fecal shedding was more positive at 3 dpi than 6 dpi. The percentage recovery of feces SENAR was 100% in 3 dpi whereas by 6 dpi, the recovery reduced to 70% in T2 and T3 and was 60% in T4.

Figure 2:
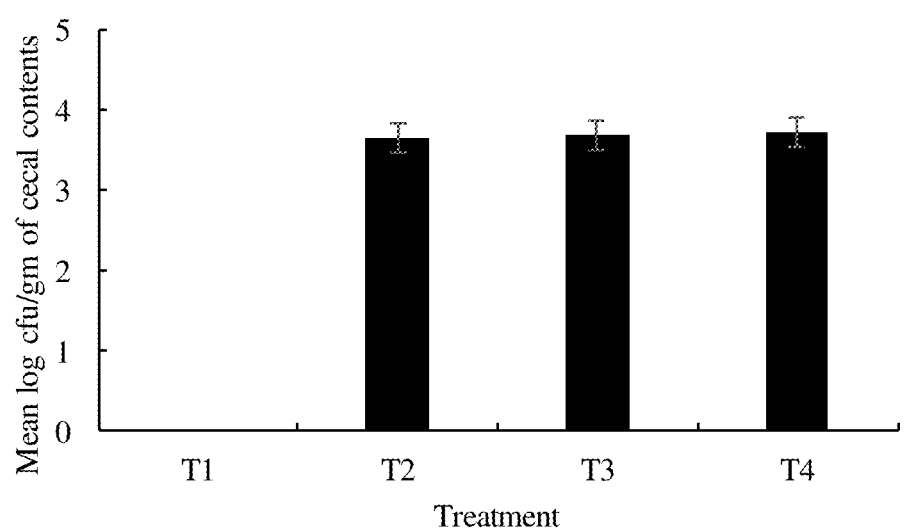
FIG. 2 shows the $SE^{NAR}$ count in ceca of laying hens supplemented with or without probiotics. The treatment groups are: T1=$SE^{NAR}$ unchallenged ($SE^{NAR}$=chicken isolate of nalidixic acid resistant *Salmonella enteritidis*), T2=$SE^{NAR}$ challenged, T3=$SE^{NAR}$ challenged+0.05% probiotics (probiotics=direct-fed microbial comprising the *Lactobacillus plantarum* strain KCCM 11453P), and T4=$SE^{NAR}$ challenged+0.1% probiotics.

All hens, including T1, were euthanized and sampled for liver with gall bladder (L/GB), ovary, spleen and ceca on 7 dpi. The negative control group T1 did not show any positive recovery in ceca throughout the experimental period (see FIG. 2). There was no reduction in the $SE^{NAR}$ colonization in the chicken ceca after supplementing two levels of probiotics. The mean $\log_{10}$ cfu/gm of cecal contents was 3.7 in T2, T3 and T4. There was no difference between the treatments with supplementation of probiotics.

Figure 3:
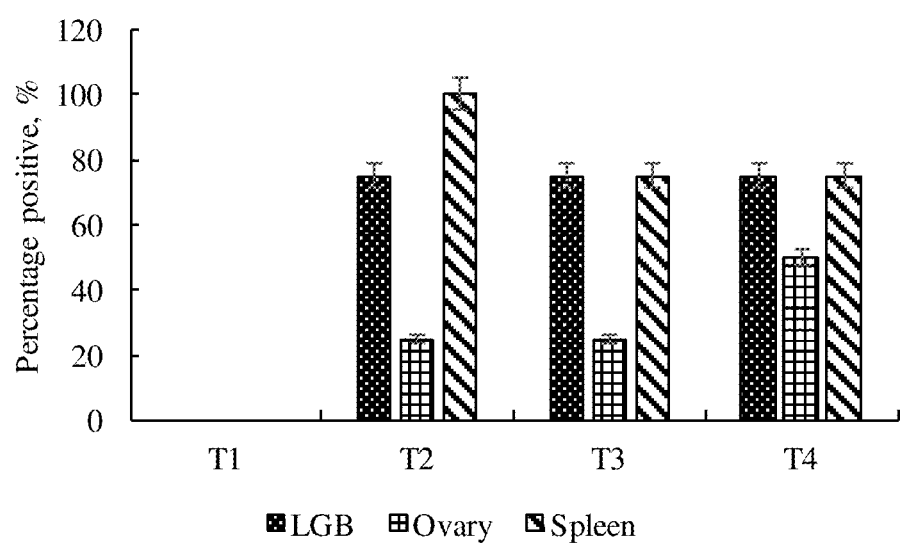
FIG. 3 shows the presence or absence of $SE^{NAR}$ in liver with gall-bladder (LGB), ovary and spleen in laying hens challenged with $SE^{NAR}$ and supplemented with or without probiotics. The treatment groups are: T1=$SE^{NAR}$ unchallenged, T2=$SE^{NAR}$ challenged, T3=$SE^{NAR}$ challenged+0.05% probiotics, and T4=$SE^{NAR}$ challenged+0.1% probiotics.

The recovery of $SE^{NAR}$ in L/GB was not different between the treatments and was 78% recovery in all 3 groups (see FIG. 3). The pattern of positive recovery of ovary was lower than L/GB or spleen. Ovary was 20% positive for $SE^{NAR}$ in T2 and T3, whereas it was 50% positive in T4. Spleen was 100% positive in T2 while it was 80% positive in T3 and T4, respectively. There was no any positive recovery in T1 group in either of the organs.

5.2 Effects of Probiotics and $SE^{NAR}$ in Immune Response in Ileum

For measurement of both pro- and anti-inflammatory cytokines such as interleukin (IL)-1B, 6, 10, interferon gamma (IFN-γ) and toll-like receptor (TLR)-4, RNA was extracted from ileum and subjected to real-time quantitative polymerase chain reaction (qRT-PCR) using the pairs of primers summarized in Table 3.

TABLE 3

Pairs of chicken cytokine primer sequences used in RT-PCR study.

| Gene[1] | Primer sequence[2] (5'-3') | Gene bank accession No. | Fragment size (bp) | Annealing Temperature (° C.) |
|---|---|---|---|---|
| GAPDH | F: GCTAAGGCTGTGGGGAAAGT (SEQ ID NO: 1) R: TCAGCAGCAGCCTTCACTAC (SEQ ID NO: 2) | K01458 | 116 | 55 |
| TLR-4 | F: TCCGTGCCTGGAGGTAAGT (SEQ ID NO: 3) R: TGCCTTGGTAACAGCCTTGA (SEQ ID NO: 4) | NM001030693 | 190 | 56 |
| IL-6 | F: CAGGACGAGATGTGCAAGAA (SEQ ID NO: 5) R: TAGCACAGAGACTCGACGTT (SEQ ID NO: 6) | AJ309540 | 233 | 59 |
| IL-10 | F: GCTCTCCTTCCACCGAAACC (SEQ ID NO: 7) R: GGAGCAAAGCCATCAAGCAG (SEQ ID NO: 8) | AJ621614 | 103 | 56 |
| IL-1B | F: CACAGAGATGGCGTTCGTT (SEQ ID NO: 9) R: GCAGATTGTGAGCATTGGGC (SEQ ID NO: 10) | NM204524 | 118 | 56 |
| IFN-γ | F: GCATCTCCTCTGAGACTGGC (SEQ ID NO: 11) R: GCTCTCGGTGTGACCTTTGT (SEQ ID NO: 12) | NM205149 | 159 | 58 |

[1]GAPDH = Glyceraldehyde-3-phosphate dehydrogenase; IL = interleukin; IFN = interferon; TLR = Toll-like receptor.

Figure 5A:
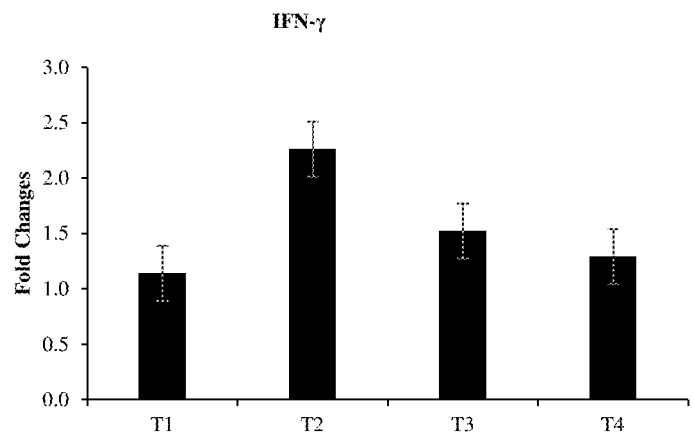
FIGS. 5A-5E shows the relative expression of IFN-γ (FIG. 5A), IL-1B (FIG. 5B), IL-6 (FIG. 5C), TLR-4 (FIG. 5D), and IL-10 (FIG. 5E) in ileum of laying hens challenged or unchallenged with $SE^{NAR}$. The treatment groups are: T1=$SE^{NAR}$ unchallenged, T2=$SE^{NAR}$ challenged, T3=$SE^{NAR}$ challenged+0.05% probiotics, and T4=$SE^{NAR}$ challenged+0.1% probiotics.
Figure 5B:
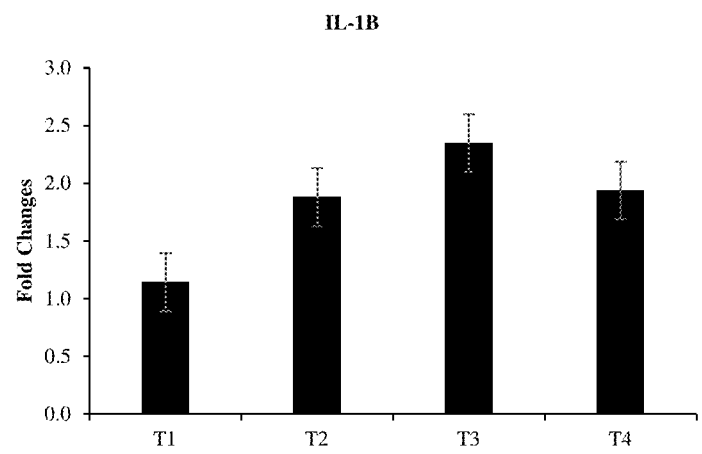
Figure 5C:
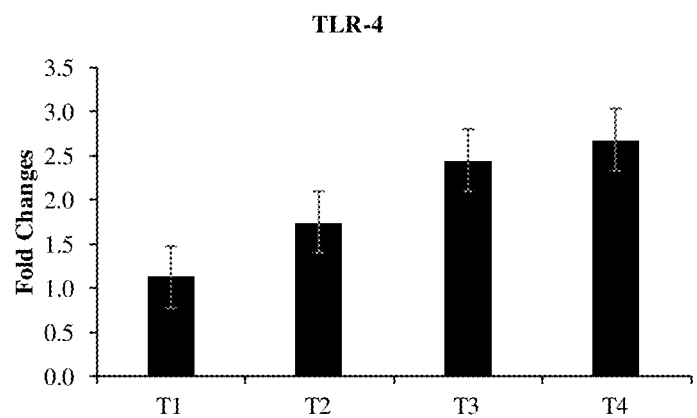
Figure 5D:
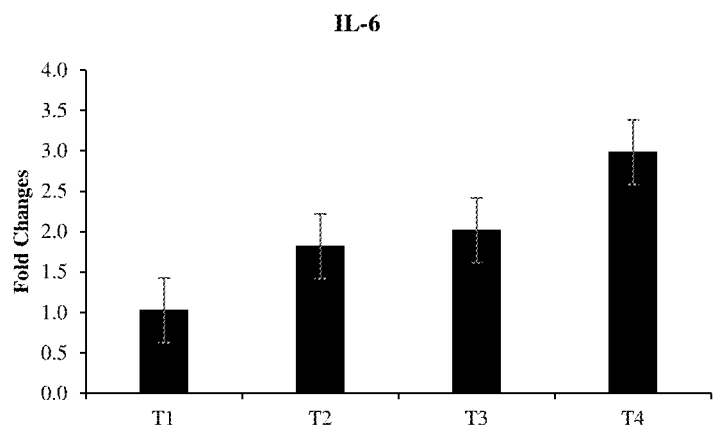
Figure 5E:
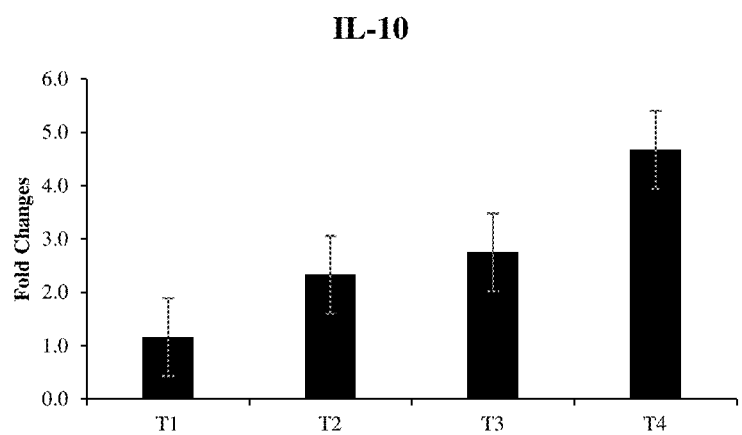

The expression was detected for all the cytokines tested and there was a significant upregulation (P<0.05) in most of the cytokines tested (FIGS. 5A-5E). There was a significant upregulation of all cytokines in T2 due to $SE^{NAR}$ challenge. Supplementation of probiotics levels either upregulated or resulted in similar level of expression of IFN-γ as T2 (FIG. 5A). T3 and T4 produced the similar expression to T1. Supplementation of probiotics showed mixed results with IL-1B in our study. There was a significant upregulation of IL-1B in T2, T3 and T4 compared to T1 (FIG. 5B). Supplementation of probiotics at T3 level increased the IL-1B at higher level in ileum. For IL-6, T4 had significantly higher expression (P<0.05) than rest of the treatment group whereas T2 was not different to T3 (FIG. 5C). However, the supplemented levels of probiotics did not reduce the expression, except for T4. The expression of TLR-4 due to $SE^{NAR}$ challenge (T2) was higher but not different to T1 (FIG. 5D). There was significant upregulation (P<0.05) of TLR-4 in both T3 and T4. Expression of IL-10 was significantly higher (P<0.05) in T2, T3 and T4 compared to T1 with the highest expression in T4 (FIG. 5E).

In sum, $SE^{NAR}$ challenge resulted in significant upregulation (P<0.05) of cytokines tested. Highest level of probiotics resulted in a significant decrease in IFN-γ and elevation of IL-10 gene expression in ileum of chickens. For the remaining cytokines tested, the supplementation of probiotics resulted in either higher or similar expression to that of $SE^{NAR}$ challenge. The studies reveal that there was some regulation of immune genes by probiotics supplementation without any bacteriological effect on internal organs or feces $SE^{NAR}$ shedding.

We claim:

1. A method for protecting an animal from pathogenic bacterial infection, comprising administering to the animal a high temperature pelleted basal diet feed supplemented with at least 0.01% by weight of a direct-fed microbial comprising *Lactobacillus plantarum* for a period of at least 7 days,
    wherein the direct-fed microbial comprises the *Lactobacillus plantarum* strain deposited with Korean Culture Center of Microorganisms (KCCM) under Accession No. KCCM 11258P and/or the *Lactobacillus* plantarum strain deposited with Korean Culture Center of Microorganisms (KCCM) under Accession No. KCCM 11453P, and
    wherein the animal fed the direct-fed microbial comprising the *Lactobacillus plantarum* strain deposited with Korean Culture Center of Microorganisms (KCCM) under Accession No. KCCM 11258P has a lower mortality rate upon infection by a pathogenic bacterium chosen from *Salmonella typhimurium, Salmonella enteritidis*, and/or *Clostridium perfringens* as compared to a corresponding control animal that is not fed with the direct-fed microbial, or
    wherein the animal fed the direct-fed microbial comprising the *Lactobacillus plantarum* strain deposited with Korean Culture Center of Microorganisms (KCCM) under Accession No. KCCM 11453P has a lower mortality rate upon infection by a pathogenic bacterium chosen from *Escherichia coli, Salmonella typhimurium, Salmonella enteritidis*, and/or *Clostridium perfringens* as compared to a corresponding control animal that is not fed with the direct-fed microbial;
    wherein the animal is a cattle, pig or poultry.

2. The method of claim 1, wherein the animal is poultry.

3. The method of claim 2, wherein the poultry is a broiler chicken or an egg-producing chicken.

4. The method of claim 2, wherein the animal is poultry and the pathogenic bacterium is chosen from avian pathogenic *Escherichia coli, Salmonella typhimurium Salmonella enteritidis*, and/or *Clostridium perfringens*.

5. The method of claim 4, wherein the poultry is a broiler chicken or an egg-producing chicken.

6. The method of claim 4, wherein the direct-fed microbial comprises the *Lactobacillus plantarum* strain deposited with Korean Culture Center of Microorganisms (KCCM) under Accession No. KCCM 11453P.

7. The method of claim 6, wherein the *Lactobacillus plantarum* is grown and concentrated by fermentation on a feed grain substrate.

8. The method of claim 7, wherein the fermentation is solid state fermentation.

9. The method of claim 1, wherein the *Escherichia coli* is avian pathogenic *Escherichia coli*.

10. The method of claim 1, wherein the direct-fed microbial comprises *Lactobacillus plantarum* strain deposited with Korean Culture Center of Microorganisms (KCCM) under Accession No. KCCM 11453P.

11. The method of claim 1, wherein the *Lactobacillus plantarum* is grown and concentrated by fermentation on a feed grain substrate.

12. The method of claim 11, wherein the fermentation is solid state fermentation.

13. The method of claim 1, wherein the high temperature pelleted basal diet feed is pelleted at a temperature range comprising about 95° C.

14. The method of claim 1, wherein the growth of pathogenic bacteria in the gastrointestinal tract of the animal is reduced.

15. The method of claim 1, wherein the direct-fed microbial comprises the *Lactobacillus plantarum* strain deposited with Korean Culture Center of Microorganisms (KCCM) under Accession No. KCCM 11258P.

16. A method for reducing the growth of pathogenic bacteria in the gastrointestinal tract of an animal, comprising administering to the animal a high temperature pelleted basal diet feed supplemented with at least 0.01% by weight of a direct-fed microbial comprising *Lactobacillus plantarum* for a period of at least 7 days,
    wherein the direct-fed microbial comprises the *Lactobacillus plantarum* strain deposited with Korean Culture Center of Microorganisms (KCCM) under Accession No. KCCM 1125813 and/or the *Lactobacillus plantarum* strain deposited with Korean Culture Center of Microorganisms (KCCM) under Accession No. KCCM 11453P,
    wherein the *Lactobacillus plantarum* is grown and concentrated by a solid state fermentation process using a feed grain substrate, and
    wherein the growth of pathogenic bacteria chosen from *Salmonella typhimurium Salmonella enteritidis*, and/or *Clostridium perfringens* in the gastrointestinal tract of the animal fed the *Lactobacillus plantarum* strain deposited with Korean Culture Center of Microorganisms (KCCM) under Accession No, KCCM 11258P is reduced as compared to a corresponding control animal that is not fed with the direct-fed microbial, or
    wherein the growth of pathogenic bacteria chosen from *Escherichia coli, Salmonella typhimurium, Salmonella enteritidis*, and/or *Clostridium perfringens* in the gastrointestinal tract of the animal fed the *Lactobacillus plantarum* strain deposited with Korean Culture Center of Microorganisms (KCCM) under Accession No. KCCM 11453P is reduced as compared to a corresponding control animal that is not fed with the direct-fed microbial;
    wherein the animal is a cattle, pig or poultry.

17. The method of claim 16, wherein the high temperature pelleted basal diet feed is pelleted at a temperature range comprising about 95° C.

18. The method of claim 16, wherein the animal is poultry.

19. The method of claim 18, wherein the poultry is a broiler chicken or an egg-producing chicken.

20. The method of claim 16, wherein the direct-fed microbial comprises *Lactobacillus plantarum* strain deposited with Korean Culture Center of Microorganisms (KCCM) under Accession No. KCCM 11453P.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
gctaaggctg tggggaaagt                                                  20

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
tcagcagcag ccttcactac                                                  20

<210> SEQ ID NO 3
<211> LENGTH: 19
<212> TYPE: DNA
<213> ORGANISM: Artificial sequence
<220> FEATURE:
<223> OTHER INFORMATION: Primer

<400> SEQUENCE: 3
tccgtgcctg gaggtaagt                                                   19

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tgccttggta acagccttga                                                  20

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
caggacgaga tgtgcaagaa                                                  20

<210> SEQ ID NO 6
<211> LENGTH: 20
<212> TYPE: DNA

<213> ORGANISM: Artificial sequence
<220> FEATURE:
<223> OTHER INFORMATION: Primer

<400> SEQUENCE: 6
tagcacagag actcgacgtt                                                       20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
gctctccttc caccgaaacc                                                       20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
ggagcaaagc catcaagcag                                                       20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
cacagagatg gcgttcgttc                                                       20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gcagattgtg agcattgggc                                                       20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
gcatctcctc tgagactggc                                                       20

<210> SEQ ID NO 12
<211> LENGTH: 20
<212> TYPE: DNA
<213> ORGANISM: Artificial sequence

```
<220> FEATURE:
<223> OTHER INFORMATION: Primer

<400> SEQUENCE: 12
gctctcggtg tgacctttgt                                          20
```